United States Patent [19]

Webb et al.

[11] Patent Number: 4,659,774

[45] Date of Patent: Apr. 21, 1987

[54] SUPPORT FOR SOLID-PHASE OLIGONUCLEOTIDE SYNTHESIS

[75] Inventors: Thomas R. Webb, Belmount, Calif.; Chien-Pin S. Hsu, King of Prussia, Pa.

[73] Assignee: American Hoechst Corporation, Somerville, N.J.

[21] Appl. No.: 794,016

[22] Filed: Nov. 1, 1985

[51] Int. Cl.$^4$ .................. C08F 8/32; C07H 21/02
[52] U.S. Cl. ..................... 525/54.2; 525/326.1; 525/326.7; 525/327.3; 525/328.2; 525/328.5; 525/333.4
[58] Field of Search .............. 525/54.2, 54.1, 54.11, 525/326.1, 326.7, 327.3, 328.2, 328.5, 333.4

[56] References Cited

U.S. PATENT DOCUMENTS 4,273,878 6/1981 Amick ............................. 525/54
4,507,433 3/1985 Miller et al. .................... 525/54.11
4,569,967 2/1986 Kornreich et al. ............... 525/54.11

OTHER PUBLICATIONS

Kaplan, *Trends in Biotechnology*, vol. 3, No. 10, 1985, pp. 253–256, "The Automatic Synthesis of Oligodeoxyribonucleotides", (Copy Supplied by Applicants in Paper No. 5).

*Primary Examiner*—John Kight
*Assistant Examiner*—Nathan M. Nutter
*Attorney, Agent, or Firm*—J. Rosenstock

[57] ABSTRACT

This invention relates to a support for oligonucleotide synthesis and more particularly to a necleoside-linker/polymer support composite having the general formula $$P'—S'$$

wherein P' is a polymer support which bears oxirane, aziridine or episulfide groups or which contains good leaving groups for nucleophilic displacement; and S' is a nucleoside-linker having the general formula $$W—(CH_2)_a—X—(CH_2)_b—Y—(CH_2)_c—Z$$

wherein W and Z each independently comprise a nucleophile; X and Y which, independently may or may not be present, comprise groups of high hydrophilicity; and a, b, c are integers from 0 to 9, wherein a plus b plus c exceeds 6.

22 Claims, No Drawings

SUPPORT FOR SOLID-PHASE OLIGONUCLEOTIDE SYNTHESIS

BACKGROUND OF THE INVENTION

Synthetic oligonucleotides of deoxyribonucleic acid (DNA) and ribonucleic acid (RNA) whose base sequences are known have become extremely useful and important through the development of molecular biology and of genetic engineering in particular. These synthetic oligonucleotides have been widely used in the isolation and synthesis of structural genes, DNA sequencing, site-specific mutagenesis and medical research.

It is well known that oligonucleotide synthesis proceeds more easily, efficiently and less expensively when the oligonucleotides are assembled on a solid support. A solid support plays a unique and crucial role in solid-phase synthesis. A kinetic study of condensation reactions indicates that the condensations follow pseudo first-order kinetics. The rate constant decreases as the coupling units increase from monomers to dimers to trimers. S. Ikuta, R. Chattopadhyaya and R. E. Dickerson, *Nucl. Acids Res.*, 12, 6511–6522 (1984). Steric hindrance and surface repulsion encountered during nucleoside addition apparently increases with larger building blocks.

In spite of many efforts studying polymer support DNA synthesis, most practical assemblies of oligonucleotides have been limited to 30–40 bases. One of the exceptions is phosphoramidite DNA synthesis on a long chain alkylamine (LCAA) controlled pore glass (CPG) solid support. S. P. Adams, K. S. Kavka, E. J. Wykes, S. B. Holder and G. R. Galluppi, *J. Am. Chem. Soc.*, 105, 661–663 (1983); G. R. Gough, M. J. Bruden and P. T. Gilham, *Tetrahedron Letters*, 4177–4180 (1981). The superiority of this support appears to be due to the introduction of a "long chain" spacer between the polymer support and the first nucleoside, in that the undesired steric hindrance and repulsion may be significantly reduced. In fact, aminopropylated CPG, which provides only a "short" spacer arm is a much less desired support as less effective nucleotide couplings were found when it was used. H. Koster, J. Berimat, J. McManus, A. Walter, A. Strimpe, Ch. K. Narang and N. D. Sinba, *Tetrahedron Letters*, 40, 103–112 (1984). Unfortunately, however, LCAA-CPG must be prepared through a multistep, labor intensive process. It is desired, therefore, to produce a relatively inexpensive, readily-available, easily prepared synthesis support which contains all of the advantages of the previously mentioned support.

SUMMARY OF THE INVENTION

This invention relates to a support for oligonucleotide synthesis and more particuarly to a nucleoside-linker/polymer support composite having the general formula

P'—S' wherein P' is a polymer support which bears oxirane, aziridine or episulfide groups or which contains good leaving groups for nucleophilic displacement; and S' is a nucleoside-linker having the general formula W—(CH$_2$)$_a$—X—(CH$_2$)$_b$—Y—(CH$_2$)$_c$—Z wherein W and Z each independently comprise a nucleophile; X and Y, which independently may or may not be present, comprise groups of high hydrophilicity; and a, b, c are integers from 0 to 9, where a plus b plus c exceeds 6.

DETAILED DESCRIPTION OF THE INVENTION

This invention relates to a support for oligonucleotide synthesis which comprises a nucleoside-linker/polymer support composite having the general formula

P'—S' wherein P' is a polymer support which bears oxiane, aziridine or episulfide groups or which contains good leaving groups for nucleophilic displacement such as halides, sulfonates, perchlorates and oxonium ions, and S' is a nucleoside-linker having the general formula W—(CH$_2$)$_a$—X—(CH$_2$)$_b$—Y—(CH$_2$)$_c$—Z wherein W and Z each independently comprise a nucleophile; X and Y, which independently may or may not be present, each comprise a group of high hydrophilicity; and a, b, c are integers from 0 to 9, where a plus b plus c exceeds 6.

Further, the invention also relates to a nucleoside/nucleoside-linker/polymer support composition having the general formula

P'—S'—N' wherein P' and S' are as defined above and N' comprises a protected nucleoside or its analog.

Preferably, the polymer support of this invention is one which bears oxirane groups, such as an oxirane resin. It is anticipated, however, that aziridine or episulfide groups on a solid support work as well for the purposes of this invention. An appropriate oxirane resin may be an oxirane polyacrylamide bead such as a co-polymer of methacrylamide, alkyl-glycidyl ether and N-methylene-bis-methacrylamide, available as Eupergit C obtained from Rohm Pharma G.m.b.H of Weiterstadt, West Germany. Such oxirane resins have several characteristics which are found to be useful in oligonucleotide synthesis supports, for instance, good flow properties with minimal swelling and shrinking due to the highly cross-linked nature of the resin and its high surface area with controlled pore size.

Although ordinary ethers do not cleave, oxiranes are cleaved quite easily to relieve their ring strain. In neutral or basic solution, nucleophile (Nu$^-$) attack more readily at the less highly substituted carbon to give the ring-opened product as illustrated in the following equation

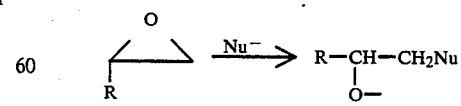

Aziridines and episulfides, three-membered rings containing, respectively, nitrogen and sulfur, are also easily cleaved in a similar fashion.

The polymer support of this invention may also be one which contains good leaving groups for nucleophilic displacement, such as cross-linked chloroalkylated polystyrene, chloroalkylated silica gel, and N-hydroxysuccinimide glycophase controlled pore glass. The nucleoside-linker (or spacer) of this invention has the general formula $$W-(CH_2)_a-X-(CH_2)_b-Y-(CH_2)_c-Z$$

wherein W and Z are each independently nucleophiles such as amine, alcohol and thiol groups; X and Y, which independently may or may not be present, are each groups of high hydrophilicity, such as NR, O, S $$\underset{O}{\overset{SR,}{\underset{\|}{\|}}} \quad \underset{S}{\overset{PR}{\underset{\|}{\|}}} \text{ and } \underset{O}{\overset{PR,}{\underset{\|}{\|}}}$$

where R is hydrogen, alkyl or aryl; and a, b, c are integers from 0 to 9, where a plus b plus c exceeds 6. Most preferably, the nucleoside-linker is 4,9-dioxa-1,12-dodecanediamine.

The nucleosides which can be used in this invention are protected nucleosides and their analogs which conform to the general formula

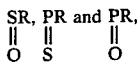

wherein P'' is a suitable protecting group for the 5' hydroxyl of a nucleoside, preferably dimethoxytrityl (DMT); P''' is hydrogen whe deoxyribonucleosides are being synthesized into oligodeoxynucleotides and O—P'''' when ribonucleosides are being synthesized into oligoribonucleotides, wherein P'''' is a suitable protecting group such as tetrahydropyranyl; B is a nucleoside base, i.e., thymine, adenine, guanine, cytosine or uracil, which may be suitably protected by groups such as benzoyl (Bz) and isobutyryl (iBu); and R' is a bifunctional group which acts as a connector between the nucleoside and the nucleoside-linker/polymer support composite, preferably succinate.

The oligonucleotide synthesis support of this invention is prepared by first forming the nucleoside-linker/polymer support composite described herein above. This may be accomplished, for instance, by treatment of an excess of the polymer support to be used with an appropriate nucleoside-linker composition to form a polymer support/nucleoside-linker composite. In doing so, the nucleoside-linker is conjugated to the polymer support through a covalent bond between the nucleophile (nucleoside-linker) and one of the oxirane's carbons or the carbon which bears the leaving group. When a support containing oxirane groups and a diamine (as the nucleoside-linker) are used, the conjugation occurs by the following scheme

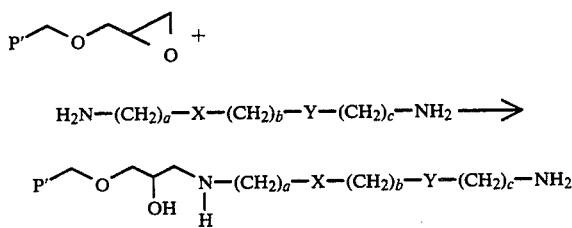

where P', X, Y, a, b, c are as defined herein above; W and Z are amines for illustrative purposes. Where W and Z are alcohols or thiols, a similar mechanism occurs, as would be readily apparent to one skilled in the art. After conjugation, there may be free polymer support remaining with the formed composite.

In preparing the nucleoside/nucleoside-linker/polymer support of this invention, nucleoside-pentachlorophenyl succinate is prepared according to methods known in the art (see, Miyoshi, Huang and Itakura, *Nucl. Acids Res.*, 8, 5491–5505 (1980).

This is then coupled to the nucleoside-linker/polymer support composite previously formed through a covalent bond in the form of an amide, ester or thioester. It is not necessary to first separate the formed composite from the remaining free polymer support. The residual oxiranes and leaving groups are exhausted by the addition of excess deactivating nucleophiles such as 2-mercaptoethanol. To avoid future complications, all the free amino, hydroxyl, sulfhydryl groups are then capped with capping reagents such as acetic anhydride, phenyl isocyanate. The desired nucleoside/nucleoside-linker/polymer support conjugate has the following formula

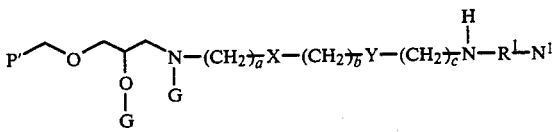

wherein G is a suitable capping group such as acetyl; the polymer support is one which contains oxirane groups where rings have been opened by nucleoside-linker; W and Z are amino groups. Also present in the mixture is capped residual polymer support/nucleoside-linker composite and capped polymer support/deactivating nucleophile conjugate such as capped polymer support/mercaptoethanol conjugate formed from residual free polymer support which may be present.

The above-described synthesis is performed simply and without the need for chromatographic separation. The oligonucleotide synthesis support thus prepared has a long chain alkylamine containing oxygen groups as the spacer. Long chain alkylamine spacers provide two advantages. First, the possible lipid-like hydrophobic adsorption found in long chain alkyl spacers without the hydrophilic atoms such as oxygens is greatly reduced. Also, steric hindrance which occurs when shorter chain spacers are used is diminished. In addition, the resulting support of this invention is uncharged.

Oligonucleotide synthesis on the support of this invention may be accomplished by conventional methods known to those skilled in the art. For instance, solid-phase phosphortriester oligonucleotide synthesis is described in Atkinson, *The Chemical Synthesis of Oligodeoxyribonucleotides*, Biotechniques, I, 6, 1983.

Simple equipments such as Manual DNA Synthesizer from Cruachem, Inc. and their synthesis protocols may be used. Oligonucleotides are synthesized in a series of assembly cycles involving three chemical reactions. In this regard, typically the protected nucleoside bound to the insoluble support of this invention is contained in a reaction column equipped with a filter disc. Treatment of the support with detritylating reagents such as zinc bromide, trichloroacetic acid and dichloroacetic acid generates free 5' hydroxyl groups on the support. Usually a 5–30 fold excess of appropriately protected monomer or dimer unit over bound nucleoside is then added to the 5' hydroxyl oligomer to drive the reaction to completion. The dehydration (coupling) reaction is usually carried out with the coupling reagent, 1-(2-mesitylenesulfonyl)-3-nitro-1,2,4-triazole (MSNT). Any 5' hydroxyl groups that have not condensed with activated nucleotide units are conveniently "capped off" as acetate using acetic anhydride catalyzed by 4-dimethylamino.

Reagents are reacted for specified times, then removed by filtration, and the support is washed with an appropriate solvent before the next reaction is performed. This method eliminates the need for chromatography after each chain-extension step, as excess reagents are simply washed away and only the nucleotide chain attached to the support is retained in the vessel.

After the appropriate number of assembly cycles, the support is treated with a solution of 2-nitrobenzaldoxime and 1,1,3,3-tetramethylguanidine in aqueous dioxane, followed by concentrated ammonia solution in a sealed tube. The resulting oligonucleotide has all the protecting groups removed except 5'-O-dimethoxytrityl group. Appropriate purification such as gel filtration and high performance liquid chromatography (HPLC) may be carried out at this stage. Further treatment with acetic acid-water affords the completely deprotected oligonucleotide.

Oligonucleotide synthesis using the support of this invention is performed via solid-phase phosphoramidite oligonucleotide synthesis. This procedure is also described in Atkinson, *The Chemical Synthesis of Oligodeoxynucleotides*, Biotechniques, I, 6, 1983. Different reactions are involved in the formation of the internucleotidic bond. The phosphoramidities, either the dimethyl, diethyl, morpholino or diisopropyl derivatives, are activated with a tetrazole and then coupled under an inert anhydrous atmosphere. The reaction is complete in less than 5 minutes using 15-20 equivalents of phosphoramidite and 60-80 equivalents of tetrazole to one equivalent of bound nucleoside. Oxidation to phosphotriester is achieved in less than 1 minute using a solution of iodine in tetrahydrofuran containing lutidine and water. The other two reactions in each assembly cycle, detritylation and capping reaction, are similar to those described in phosphotriester synthesis.

The percent coupling yields of either of the above described synthesis procedures may be calculated by collecting and assaying spectrophotometrically an aliquot in each detritylation step since solutions containing the dimethoxytrityl cation are bright orange.

The following specific descriptions are given to enable those skilled in the art to more clearly understand and practice the invention. They should not be considered as limitations on the scope of the invention but merely as being illustrative and representative thereof.

EXAMPLE 1

Synthesis of Oxirane Resin/Nucleoside Linker Composite

Eupergit C brand resin (700 mg) was added to 3.4 ml of 0.021M aqueous solution of 4,9-dioxa-1,12-dodecanediamine. The mixture was shaken for 2 hours at room temperature, then filtered and washed successively six times with water (10 ml) and ethanol ($6 \times 10$ ml). The resulting resin was dried in vacuo at room temperature for 60 hours. The quantitation of amino group and therefore the loading of nucleoside-linker on Eupergit C resin was determined by picric acid assay, as described by Ginsin, *Anal. Chim. Acta.*, 58, 278 (1972).

EXAMPLE 2

Synthesis of Oxirane Resin/Nucleoside-Linker/Nucleoside Composite

The resin support (135 mg) prepared as in Example 1 was added to a solution of 3'-O-pentachlorophenylhemisuccinyl-5'-O-dimethoxytrityl-2'-deoxythymidine (58 mg) and triethylamine (9.75 ul) in N,N-dimethylformamide (0.6 ml). The mixture was shaken at room temperature for 22 hours. Thereafter it was filtered. The resin was washed successively with N,N-dimethylformamide ($5 \times 2$ ml), ethanol ($3 \times 2$ ml), water ($3 \times 2$ ml) and 0.01M sodium phosphate buffer pH 8.35 ($10 \times 2$ ml). The resin was added to 4.5% 2-mercaptoethanol aqueous solution (1 ml) and the mixture was shaken at room temperature overnight (15 hours). This mixture was filtered and the residue washed successively with water ($8 \times 2$ ml), ethanol ($5 \times 2$ ml) and diethyl ether ($3 \times 2$ ml). The resulting resin was dried in vacuo at room temperature for 1 hour. To this resin was added acetic anhydride (0.25 ml) and 0.2M 4-dimethylaminopyridine in 9:1 tetrahydrofuran-pyridine (0.75 ml). The mixture was shaken at room temperature and filtered. The residue was washed successively with tetrahydrofuran ($5 \times 2$ ml), pyridine ($5 \times 2$ ml), ethanol ($5 \times 2$ ml) and diethyl ether ($3 \times 2$ ml). The resin was dried in vacuo at room temperature for 17 hours.

The quantitative assay for the trityl cation and therefore the loading of nucleosides on Eupergit C resin was carried out using standard procedure, as described by Ito et al, *Nucl. Acids Res.*, 10, 1755 (1982). The loading was measured as 24 micromoles of nucleoside (2'-deoxythymidine) per gram of dry resin.

EXAMPLE 3

Phosphotriester Oligonucleotide Synthesis

A manual DNA Synthesizer manufactured by Cruachem, Inc. was utilized. The apparatus was designed to allow the solvents and the reagents being pressurized to flow through the column where the resin support is placed (flow rate: @1 ml/min.).

The basic steps employed to assemble olignucleotide include 1. flushing the column successively with pyridine (6 minutes) and 1,2-dichloroethane (4 minutes);

2. detritylation with 10% trichloroacetic acid in 1,2-dichloroethane (2 minutes), followed by flushing with 1,2-dichloroethane (3 minutes);

3. flushing successively with N,N-dimethylformamide (6 minutes) and pyridine (6 minutes);

4. introducing a solution of 5'-dimethoxytrityl-2'-deoxynucleoside-3'-O-(2-chlorophenyl)phosphate triethylammonium salt (0.04 mmol) and 1-(2-mesitylenesulfonyl-3-nitro-1,2,4-triazole (0.2 mmol) in 0.32 ml of 0.12M 3-nitro-1,2,4-triazole in pyridine, then allowing it to stand for 45 minutes; and 5. capping of any unreacted hydroxyl by introducing 0.1 ml of acetic anhydride, allowing it to stand for 2 minutes, injecting 0.15 ml of 0.2M 4-dimethylaminopyridine in 9:1 tetrahydrofuran-pyridine and allowing it to stand for 3 minutes.

All steps were performed at room temperature. The resin support (57 mg) prepared as in Example 2 was used and the aforesaid procedure was repeated 7 times to obtain a 8-base oligonucleotide d(T-A-G-C-C-T-C-

T) with a 39% overall trityl yield. The average stepwise trityl yield is 87%.

EXAMPLE 4

Removal of oligonucleotides from the support and analysis of the product

The resin (42 mg, prepared as in Example 3) which contains the product deoxyoligonucleotide was added into a solution prepared by dissolving 2-nitrobenzaldoxime (142 mg) in p-dioxane (1 ml) and water (1 ml), followed by 1,1,3,3-tetramethylguanidine (0.1 ml). The resulting mixture was mixed briefly by vortexing and allowed to stand at room temperature for 28 hours. The resin was removed by filtration and washed with water (3×1 ml). The combined filtrate and washings was concentrated in vacuo, redissolved, in concentrated ammonium hydroxide (5 ml) and heated at 58°–64° C. for 9 hours in a sealed 10 ml ampule. It was concentrated in vacuo to afford the 5'-O-dimethoxytrityl-deoxyoligonucleotide. It was partitioned between 0.01M triethylammonium bicarbonate (1 ml) and diethyl ether (2 ml). The aqueous layer was washed with more diethyl ether (5×2 ml) and subjected to Sephadex G-50 gel filtration (2.6×18 cm). The eluting buffer was 0.01M triethylammonium bicarbonate. Fractions (60×1.6 ml) were collected and their absorbance at 260 nm measured. (The oligonucleotide was eluted in the void volume). Fraction #21 (0.6 ml, the leading portion of the oligonucleotide peak) was first concentrated in vacuo and further detritylated with acetic acid-water (4:1, v/v) at room temperature for 30 minutes. This solution was concentrated at room temperature in vacuo, redissolved in water (1 ml) and washed with diethyl ether (3×2 ml) to give the completely deprotected deoxyoligonucleotide. Its 5'-hydroxyl is phosphorylated using [γ-32P] ATP and T4 polynucleotide kinase. Approximately 0.5–1 mg of sample was used. The crude phosphorylated product was subjected to 20% polyacrylamide gel electrophoresis using standard procedures.

We claim:

1. A polymer support/nucleoside-linker composite having the general formula

wherein P' is a polymer support which bears oxirane, aziridine or episulfide groups; S' is a nucleoside-linker having the general formula

wherein W and Z each independently comprise a nucleophile selected from the group consisting of amine, alcohol and thio groups; X and Y, which independently may or may not be present, comprise groups of high hydrophilicity; and a, b, c are integers from 0 to 9, where a plus b plus c exceeds 6; wherein P' is conjugated through a carbon thereof to S' by means of a covalent bond with either of said nucleophile W or Z.

2. The polymer support/nucleoside-linker composite of claim 1 wherein said polymer support bears oxirane groups.

3. The polymer support/nucleoside-linker composite of claim 2 wherein said polymer support is an oxirane resin.

4. The polymer support/nucleoside-linker composite of claim 3 wherein said oxirane resin comprises an oxirane polyacrylamide bead.

5. The polymer support/nucleoside-linker composite of claim 4 wherein said oxirane polyacrylamide bead consists of a copolymer of methacrylamide, alkyl glycidyl ether and N-methylene-bis-methacrylamide.

6. The polymer support/nucleoside-linker composite of claim 1 wherein said nucleophiles consist of amine groups.

7. The polymer support/nucleoside-linker composite of claim 1 wherein said groups of high hydrophilicity are selected from the group consisting of NR, O, S,

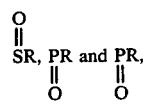

wherein R is hydrogen, alkyl or aryl.

8. The polymer support/nucleoside-linker composite of claim 7 wherein said groups of high hydrophilicity consist of oxygen.

9. A support for solid phase oligonucleotide synthesis comprising a polymer support/nucleoside-linker/nucleoside composite having the general formula

wherein P' is a polymer support which bears oxirane, aziridine or episulfide groups; S' is a nucleoside-linker having the general formula

wherein W and Z each independently comprise a nucleophile selected from the group consisting of amine, alcohol and thio groups; X and Y, which independently may or may not be present, comprise groups of high hydrophilicity; and a, b, c are integers from 0 to 9, where a plus b plus c exceeds 6; N' is a protected nucleoside or its analog; and wherein P' is conjugated through a carbon thereof to S' by means of a covalent bond with either of said nucleophile W or Z.

10. The support for solid phase oligonucleotide synthesis of claim 9 wherein said polymer support bears oxirane groups.

11. The support for solid phase oligonucleotide synthesis of claim 10 wherein said polymer support is an oxirane resin.

12. The support for solid phase oligonucleotide synthesis of claim 11 wherein said oxirane resin comprises an oxirane polyacrylamide bead.

13. The support for solid phase oligonucleotide synthesis of claim 12 wherein said oxirane polyacrylamide bead consists of a copolymer of methacrylamide, alkyl glycidyl ether and N-methylene-bis-methacrylamide.

14. The support for solid phase oligonucleotide synthesis of claim 9 wherein said nucleophiles consist of amine groups.

15. The support for solid phase oligonucleotide synthesis of claim 9 wherein said groups of high hydrophilicity are selected from the group consisting of NR, O, S,

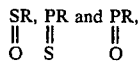

wherein R is hydrogen, alkyl or aryl.

16. The support for solid phase oligonucleotide synthesis of claim 15 wherein said groups of high hydrophilicity consist of oxygen.

17. The support for solid phase oligonucleotide synthesis of claim 9 wherein said protected nucleoside conforms to the general formula

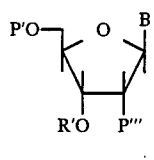

wherein P" is a suitable protecting group for the 5' hydroxyl of a nucleoside; P'" is hydrogen or O—P"", where P"" is a suitable protecting group; B is a nucleoside base; and R is a bifunction group which acts as a connector between said nucleoside and said nucleoside-linker/polymer support composite.

18. The support for solid phase oligonucleotide synthesis of claim 17 wherein P" is dimethoxytrityl.

19. The support for solid phase oligonucleotide synthesis of claim 17 wherein P"" is tetrahydropyranyl.

20. The support for solid phase oligonucleotide synthesis of claim 17 wherein said nucleoside base is suitably protected.

21. The support for solid phase oligonucleotide synthesis of claim 20 wherein said nucleoside base is protected by a group selected from the group consisting of benzoyl and isobutyryl.

22. The support for solid phase oligonucleotide synthesis of claim 17 wherein R' consists of succinate.

* * * * *

UNITED STATES PATENT AND TRADEMARK OFFICE
CERTIFICATE OF CORRECTION

PATENT NO. : 4,659,774

DATED : April 21, 1987

INVENTOR(S) : Chien-Pin S. Hsu, et al

It is certified that error appears in the above-identified patent and that said Letters Patent is hereby corrected as shown below:

On the title page:

[75] Inventors: should read --
Chien-Pin S. Hsu, King of Prussia, Pa.;
Thomas R. Webb, Belmount, Calif. --.

Signed and Sealed this

Thirty-first Day of May, 1988

Attest:

DONALD J. QUIGG

*Attesting Officer*     *Commissioner of Patents and Trademarks*